(12) United States Patent
Puschett

(10) Patent No.: US 7,439,071 B2
(45) Date of Patent: Oct. 21, 2008

(54) METHOD OF EMPLOYING ELEVATION OF MARINOBUFAGENIN IN DETERMINING THE PRESENCE OF PREECLAMPSIA AND RELATED APPARATUS

(75) Inventor: Jules B. Puschett, New Orleans, LA (US)

(73) Assignee: The Administrators of the Tulane Educational Fund, New Orleans, LA (US)

( * ) Notice: Subject to any disclaimer, the term of this patent is extended or adjusted under 35 U.S.C. 154(b) by 12 days.

(21) Appl. No.: 10/544,468

(22) PCT Filed: Feb. 2, 2004

(86) PCT No.: PCT/US2004/002802

§ 371 (c)(1),
(2), (4) Date: Jun. 16, 2006

(87) PCT Pub. No.: WO2004/071273

PCT Pub. Date: Aug. 26, 2004

(65) Prior Publication Data

US 2006/0263891 A1 Nov. 23, 2006

Related U.S. Application Data

(60) Provisional application No. 60/444,730, filed on Feb. 4, 2003.

(51) Int. Cl.
*G01N 33/00* (2006.01)
*G01N 33/48* (2006.01)

(52) U.S. Cl. .............................. 436/87; 436/63; 436/65

(58) Field of Classification Search .................. 436/63, 436/65, 87; 422/61
See application file for complete search history.

(56) References Cited

U.S. PATENT DOCUMENTS

| 5,079,171 | A | 1/1992 | Senyei et al. |
| 5,543,138 | A | 8/1996 | Keith |
| 5,770,376 | A | 6/1998 | Bagrov |
| 2003/0044856 | A1 | 3/2003 | Puschett |
| 2006/0134106 | A1 * | 6/2006 | Adair ...................... 424/133.1 |

OTHER PUBLICATIONS

Bagrov, Alexei Y., et al., "Characterization of a Urinary Bufodienolide Na+, K+-ATPase inhibitor in Patients After Acute Myocardial Infarction," Hypertension, vol. 31, No. 5, pp. 1097-1103, May 1998.

Chen, Tai C., et al., "Volume Expansion-Induced Changes in Renal Tubular Membrane Protein Phosphorylation," Biochemical and Biophysical research Communications, vol. 143, No. 1, pp. 74-80, Feb. 1987.

Lopatin, D.A. et al., "Circulating Bufodienolide and Cardenolide Sodium Pump Inhibitors in Preeclampsia," Journal of Hypertension, 1999, vol. 17, No. 8, pp. 1179-1187.

Khedun, S.M. et al., "Drug Management of Hypertensive Disorders or Pregnancy," Pharmacol. Ther., 1997, vol. 74, No. 2, pp. 221-258.

* cited by examiner

*Primary Examiner*—Maureen M Wallenhorst
(74) *Attorney, Agent, or Firm*—Carol A. Marmo; Arnold B. Silverman; Eckert Seamans Cherin & Mellott, LLC

(57) ABSTRACT

A method of determining the presence of preeclampsia is provided wherein a determination is made as to whether there has been a substantial elevation in marinobufagenin which may be a blood-derived or urine-derived and if such elevation does exist concluding that preeclampsia does exist in a patient. The method may advantageously be practiced by employing urine, blood serum or blood plasma as the body specimen containing the protein in determining whether a patient has preeclampsia. The method may include subsequent therapeutic patient treatment. Related diagnostic apparatus is also provided.

11 Claims, No Drawings

METHOD OF EMPLOYING ELEVATION OF MARINOBUFAGENIN IN DETERMINING THE PRESENCE OF PREECLAMPSIA AND RELATED APPARATUS

CROSS-REFERENCE TO RELATED APPLICATION

The present application claims the benefit of International Application No. PCT/US2004/002802, filed Feb. 2, 2004, entitled "Method of Employing Elevation of Marinobufagenin in Determining the Presence of Preeclampsia and Related Apparatus," which claims the benefit of U.S. Provisional Patent Application Ser. No. 60/444,730, filed Feb. 4, 2003, entitled "Method of Employing Elevation of Marinobufagenin in Determining the Presence of Preeclampsia and Related Apparatus."

BACKGROUND OF THE INVENTION

1. Field of the Invention

The present invention provides a means for determining whether a patient has preeclampsia and, more specifically, it provides such a method based upon the elevation of marinobufagenin in a body specimen of a pregnant woman. The invention also relates to a diagnostic apparatus employable in making such determination.

2. Description of the Prior Art

Eclampsia, which is a condition experienced by pregnant women and generally involves coma and/or convulsive seizures during the same period without other etiology. Preeclamnpsia, if untreated, can progress suddenly to eclampsia Eclampsia, which is usually fatal if untreated.

Preeclampsia is generally characterized by the presence of hypertension proteinuria and edema. It is a disorder which generally occurs only in women who are more than 20 weeks pregnant.

Elevated blood pressure or hypertension has long been recognized as a health problem. It is a very common disease which can have widespread effects on a patient's body and frequently, unlike numerous other diseases, is asymptomatic.

Despite known means of measuring blood pressure of a patient as by a sphygmomanometer, for example, there is lacking an accurate reliable means of detecting the presence of volume dependent hypertension involving higher arterial blood pressure by use of a body specimen, such as blood serum or blood plasma.

From a pathogenic standpoint, essential hypertension may be divided into two broad categories: (a) volume expansion hypertension, and (b) vasoconstriction hypertension. It has been estimated that about 30 to 40 percent of human essential hypertension may be permanently related to volume expansion hypertension, especially in certain demographic groups. Previous studies participated in by the present inventor have demonstrated an alteration in the phosphorylation of a proximal tubular membrane protein following acute saline expansion of the experimental rat (Puschett et al. Volume Expansion Induced Changes in Renal Tubular Membrane Protein Phosphorylation, Biochem. Biophys. Res. Commun., 143:pp. 74-80 (1987)).

U.S. Pat. No. 5,770,376 discloses the use of a blood specimen in diagnosing hypertension as an indication of acute myocardial infarction. It employs plasma levels of a marinobufagenin-like immunoreactivity as a marker for hypertension.

U.S. patent application Ser. No. 10/109,203, now abandoned discloses a substantial reduction in phosphorylation or concentration of a specific protein obtained from a body specimen to determine the presence of preeclampsia.

U.S. patent application Ser. No. 09/990,432, now abandoned filed Nov. 21, 2001 in the name of the present inventor, the disclosure of which is expressly incorporated herein by reference, discloses the use of the CLAMP protein in effecting a determination of the presence of chronic volume dependent hypertension.

While there is no hard and fast rule regarding diagnosis of preeclampsia, several standards have been applied. If a pregnant women develops a blood pressure of 140/90, and has edema of the face or hands, and the presence of urinary protein in concentrations greater than 0.3 grams in a 24 hour urine collection, this is generally indicative of the presence of preeclampsia.

There remains, therefore, a very real and substantial need for a method and apparatus for effectively determining the presence of preeclampsia in a pregnant patient.

SUMMARY OF THE INVENTION

The present invention has met the above-described need by providing a method of determining the presence of preeclampsia in a patient which includes whether there has been a substantial elevation in marinobufagenin in blood-derived or urine-derived specimens and, if such elevation does exists, concluding that eclampsia exists.

It is preferred that the elevation in marinobufagenin exceed about 100 to 200 percent and preferably be at least about 50 to 75 percent before making a determination that such elevation leads to the conclusion that preeclampsia exists. Urine or a blood component, such as blood serum or blood plasma containing the blood protein, may be employed in the practice of the method of the present invention.

After a determination of the presence of preeclampsia, one may employ any desired means of treating the patient to effect reduction of the same, while periodically monitoring progress.

The invention also contemplates apparatus for determining the presence of preeclampsia in a patient, which includes a specimen receiver containing a urine-derived or blood-derived specimen and an analyzer for determining if marinobufagenin is substantially elevated. The blood specimen may be blood serum or blood plasma.

It is the object of the present invention to provide a method and associated apparatus for determining the presence of preeclampsia in a patient in a reliable and rapid manner.

It is further an object of the present invention to provide apparatus, which facilitates such a determination and may employ a patient body specimen, such as blood serum, blood plasma or urine.

It is yet another object of the present invention to provide such a diagnostic system which will rely on the presence of a substantial elevation in marinobufagenin in effecting a determination that preeclampsia exists.

It is another object of the present invention to provide such a method and related apparatus, which is economical and may be practiced by paraprofessional personnel in an accurate manner.

It is a further object of the present invention to employ a determination of marinobufagenin concentration at various stages of pregnancy to both serve as a diagnostic test of preeclampsia, and also an early warning sign of potential later development of the disorder.

These and other objects of the invention will be more fully understood from the following description of the invention on reference to the illustrations appended hereto.

DESCRIPTION OF THE PREFERRED EMBODIMENTS

As used herein, the term "patient" refers to human beings.

The term "body specimen" means a specimen obtained from a patient which contains marinobufagenin and expressly includes blood serum, blood plasma and urine.

As employed herein, a reference to determining the "presence of preeclampsia" shall also be deemed to embrace also a determination of the presence of eclampsia.

The term "substantial elevation" as referred to marinobufagenin concentration as employed herein means an elevation above the normally anticipated range of marinobufagenin elevation in a pregnant person.

Preeclampsia is a disorder generally confined to women who are more than 20 weeks pregnant. It consists in the development of hypertension and proteinuria, generally in the form of albuminuria, and the supervention of excessive edema.

It is currently believed by the present inventor that preeclampsia is another example of volume expansion mediated hypertension differing from that seen in any essential hypertension only in that the kidney is under stress related to the pregnancy. Patients may have a genetic or acquired defect in the ability of their kidneys to excrete a sodium load. This deficiency may not become evident until the patient experiences the stress associated with pregnancy. As they are unable to excrete salt normally they develop volume expansion mediated hypertension. As a result of this deficiency in sodium transport in their kidneys, the salt tends to accumulate thereby causing hypertension and edema. This volume expansion is believed to cause the elaboration of the natriuretic factor known as marinobufagenin which is employed in the present invention as a marker for diagnosing preeclampsia, as well as being employed in the apparatus and therapeutic method of the present invention.

Marinobufagenin is a cardiotonic steroid which has vasoconstrictor properties. It is an inhibitor of the enzyme Na/K ATPase. It is unable to cause the excess sodium to be excreted as a result of the deficiency referred to herein above in the sodium transport pathway.

In preeclampsia, the fluid is mostly in the interstitial space where it has leaked from the intravascular space. It is believed by the present inventor that the circulating factor has a role in this "leakiness" of the vascular tree. The uterine vasculature of the preeclamptic patient is characterized by the failure of the decidual small arterioles to dilute normally thereby resulting in large bore, low resistance channels that nourish the placenta and fetus. Instead, these arterioles remain small diameter, high resistance vessels, a condition that is believed by the present inventor to result from the effects of the circulating factor. The net result is that decreased uteroplacental perfusion occurs causing intrauterine growth restriction, prematurity, and fetal wastage.

Tests performed on rat models of preeclampsia have resulted in the conclusion that marinobufagenin is mildly elevated in normal pregnancy, as the pregnancy is an example of natural volume expansion. It is elevated substantially more in preeclamptic rats. Dissecting of the individual vessels from the preeclamptic rats resulted in the determination that when vessels from normal pregnant animals or rats are perfused with marinobufagenin, they do not constrict, while perfusion of vessels from preeclamptic rats with marinobufagenin results in constriction that averages about 36 percent as compared with the controlled circumstance.

The preferred practice of the present invention for determining the presence of preeclampsia includes determining if there has been a substantial elevation in marinobufagenin concentration of the blood-derived or urine-derived specimen. The base line for such evaluations may be obtained through evaluation of normal pregnant human patients. If such elevation of marinobufagenin does exist, it is concluded that preeclampsia exists. The method provides a method capable of making this determination independently of whether vasoconstriction hypertension or other types of hypertension exists in the patient.

In general, it is preferred that a substantial elevation in marinobufagenin from normal range be deemed to be at least about a 50 percent in marinobufagenin concentration above the limit of the range of normal human patients before it is determined that preeclampsia exists, and preferably an elevation in the range of at least about 100 to 200 percent elevation. This elevation is ascertained by determining the marinobufagenin concentration of the patient's body and comparing it with an established normal specimen range.

The body specimen employed in practicing the method of the present invention may advantageously be urine or a blood-derived specimen, such as blood serum or blood plasma.

Patients with preeclampsia are volume expanded, but the majority of the excess fluid is in the interstitial rather than the intravascular compartment.

In the event that it is determined that a patient has preeclampsia after completion of the diagnostic evaluation, the patient may be treated in any therapeutically beneficial manner. Among the currently preferred treatments, after the presence of preeclampsia is confirmed, are at least one treatment from the group consisting of administering a magnesium-containing drug, administering alphamethyldopa, bed rest and delivery of the baby. Among the suitable magnesium-containing compounds is magnesium sulfate. A suitable alphamethyldopa is that, sold under the trade designation Aldomet. It is desired to resist delivery as long as possible without assuming an undue risk of the adverse consequences of eclampsia It will be appreciated that the present invention focuses on the detection of the presence of preeclampsia with subsequent treatment of the patient along any desired lines being affected once the presence of preeclampsia has been confirmed.

Another approach to therapy would be to employ antibodies to marinobufagenin as by injecting an appropriate amount into the patient at predetermined frequencies.

The apparatus of the present invention may include a specimen receiver for a patient's body blood serum, or blood plasma specimen, or urine specimen, which may be one or more suitably sized and shaped containers or multiple recesses in a tray or the like containing the specific blood-derived protein or urine-derived protein and means for determining if the protein has substantially reduced phosphorylation or concentration.

The apparatus, which may be a kit, preferably has means for determining the concentration of marinobufagenin or if a marinobufagenin elevation exceeds about 100 to 200 percent or within the range of at least about 50 to 75 percent. If the elevation exceeds these numerical standards, this indicates that preeclampsia exists in the patient If desired, automated equipment may be employed to effect or assist with the determination.

It will be appreciated that the present invention provides methods and related apparatus for employing a patient's blood or urine and determining whether preeclampsia exists in the patient, thereby permitting appropriate therapeutic measures to be taken. The system is particularly important in view of the potential life threatening nature of eclampsia as well as maternal morbidity and fetal wastage coupled with the fact that patients are frequently asymptomatic for a period of time.

The invention also contemplates a method for making such determination and providing therapeutic treatment to a patient as by administering appropriate medication with the dosage corresponding to the other health considerations regarding the patent and the severity of the preeclampsia volume dependent hypertension and the health of the patient in any other respects.

The invention also provides apparatus which may be in kit form for determining the presence of preeclampsia in a patient which includes apparatus for receiving a patient specimen containing a blood-derived marinobufagenin or urine-derived marinobufagenin and apparatus for determining if the marinobufagenin has substantially increased concentration as compared with a normal pregnant patient. Before a determination is made that preeclampsia does or does not exist, it is preferred that the substantially increased marinobufagenin concentration be deemed to be at least 50 percent and most preferably at least about 100 to 200 percent.

The method and apparatus of the present invention is not only employable to make an initial determination of whether a patient has preeclampsia, but also for subsequent monitoring of the effectiveness of therapy employed to treat this condition.

Whereas particular embodiments of the invention have been described herein for purposes of illustration, it will be evident to those skilled in the art that numerous variations of the details may be made without departing from the invention as defined in the appended claims.

I claim:

1. A method of determining the presence of preeclampsia in a patient comprising:
    obtaining a body specimen from the patient containing a marinobufagenin,
    employing urine as said body specimen,
    detecting the level of marinobufagenin in said urine body specimen, and
    comparing the level of said marinobufagenin relative to a range in normal patients, whereby a substantial elevation in marinobufagenin from the normal range is indicative of the presence of preeclampsia,
    said substantial elevation in marinobufagenin is determined to exist when said elevation is at least about 50 percent above the range in normal patients.

2. The method of claim 1 wherein the substantial elevation in marinobufagenin relative to normal patient range is indicative of preeclampsia regardless of the presence or absence of vasoconstriction.

3. The method of claim 1 wherein said substantial elevation in marinobufagenin is determined to exist when said elevation is about 100 to 200 percent above the range of normal patients.

4. The method of claim 1 wherein the presence of a substantial elevation in marinobufagenin relative to the normal patient range is indicative of the existence of preeclampsia regardless of the presence or absence of cyclic AMP.

5. The method of claim 1 wherein the presence of a substantial elevation in marinobufagenin relative to the normal patient range is indicative of preeclampsia regardless of the presence or absence of other types of hypertension in said patient.

6. An apparatus for determining the presence of preeclampsia in a patient comprising:
    a specimen receiver for receiving a body specimen from the patient containing marinobufagenin,
    said specimen receiver for receiving the body specimen from the patient being structured to employ urine as said body specimen, and
    an analyzer for determining the level of marinobufagenin relative to a range in normal patients and for determining whether a substantial elevation in marinobufagenin exists in the specimen from the patient relative to the normal range wherein the presence of a substantial elevation in marinobufagenin from the normal range is indicative of preeclampsia, and
    said analyzer for determining that a substantial elevation exists if said elevation in marinobufagenin is at least about 50 percent above the range of normal patients.

7. The apparatus of claim 6 including:
    said analyzer for determining that a substantial elevation exists if said elevated marinobufagenin is at least about 100 to 200 percent above the range of normal patients.

8. A method for determining the presence of preeclampsia in a patient and therapeutically treating the same comprising:
    determining if there is a substantial elevation of marinobufagenin in a body specimen from the patient,
    employing urine as the body specimen, and
    if such a substantial elevation does exist, treating said patient therapeutically for said preeclampsia,
    wherein said substantial elevation in marinobufagenin is determined to exist when said elevation of marinobufagenin is at least 50 percent greater than a range of normal patients.

9. The method of claim 8 including:
    employing as said therapeutic treating at least one treatment from the group consisting of administering a magnesium-containing drug, administering alphamethyldopa, bed rest and delivery of a baby from the patient.

10. The method of claim 9 including: co-administering a magnesium-containing drug and alphamethyldopa.

11. The method of claim 8 including:
    employing an antibody to marinobufagenin in said therapeutic treatment.

* * * * *